US006599530B2

United States Patent
Vahervuo

(10) Patent No.: US 6,599,530 B2
(45) Date of Patent: Jul. 29, 2003

(54) ORAL COMPACTED COMPOSITION COMPRISING CATECHOL DERIVATIVES

(75) Inventor: Kari Vahervuo, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/152,263

(22) Filed: Sep. 14, 1998

(65) Prior Publication Data

US 2002/0132009 A1 Sep. 19, 2002

(51) Int. Cl.[7] ................................ A61K 9/20
(52) U.S. Cl. .................. 424/464; 424/465; 424/488; 514/676; 514/678; 514/689; 514/772; 514/781
(58) Field of Search ................ 424/464, 465, 424/488; 514/676, 678, 689, 772, 781

(56) References Cited

U.S. PATENT DOCUMENTS 5,380,535 A * 1/1995 Geyer et al. ................ 424/484
5,446,194 A * 8/1995 Backstrom et al. ......... 558/401
5,489,614 A * 2/1996 Korkolainen et al. ....... 514/676

OTHER PUBLICATIONS

Remington: The science and practive of pharmacy. 19th Edition 1995. Mack Publishig Company Ed: Gennaro. pp. 1619–1626.*

A. Wade and P. J. Weller, Croscarmellose Sodium, *Handbook of Pharmaceutical Excipients*, Second Edition, The Pharmaceutical Press, London, 1994, 141–142.

Co–pending U.S. application No. 09/787,027, filed on Jun. 25, 2001.

Fielder, "Lexikon Der Hilfsstoffe" Editio Canteor Verlag, Aulendorf, Germany XP 002126381, 1996.

Co–pending U.S. application No. 09/605,529, filed on Jun. 29, 2000.

* cited by examiner

*Primary Examiner*—Thurman K. Page
*Assistant Examiner*—Lakshimi Channavajjala
(74) *Attorney, Agent, or Firm*—Finnegan, Henderson, Farabow, Garrett & Dunner, LLP

(57) ABSTRACT

The present invention relates to an oral compacted composition comprising entacapone, nitecapone, or a pharmaceutically acceptable salt thereof and croscarmellose sodium. The composition is premised on the discovery that croscarmellose sodium increases the release rate of entacapone or nitecapone from an oral compacted composition. Preferably the amount of croscarmellose sodium in the composition is at least 6% by weight, preferably from about 8% to about 16% by weight, especially from about 10% to about 14% by weight.

20 Claims, 2 Drawing Sheets

ORAL COMPACTED COMPOSITION COMPRISING CATECHOL DERIVATIVES

BACKGROUND OF THE INVENTION

The present invention relates to a new pharmaceutical composition comprising a catechol derivative and croscarmellose sodium as a dissolution enhancing agent. Accordingly, the present invention relates to an oral compacted composition comprising entacapone, nitecapone, or a pharmaceutically acceptable salt thereof, and croscarmellose sodium (Ac—Di—Sol) as a dissolution enhancing agent. Particularly, the invention relates to an oral compacted composition comprising entacapone, nitecapone, or a pharmaceutically acceptable salt thereof and croscarmellose sodium, wherein the amount of croscarmellose sodium in the composition is at least 6% by weight, more preferably from about 8% to about 16% by weight, especially from about 10% to 14% by weight. Preferably the oral compacted composition is in the form of a tablet. Further, the present invention relates to a method of preparing an oral compacted composition comprising entacapone, nitecapone, or pharmaceutically acceptable salt thereof, and croscarmellose sodium. The present invention also relates to the use of croscarmellose sodium in the manufacture of an oral compacted composition comprising entacapone, nitecapone, or a pharmaceutically acceptable salt thereof.

The chemical names of entacapone and nitecapone are (E)-2-cyano-3-(3,4-dihydroxy-5-nitrophenyl)-N,N-diethyl-2-propenamide and 3-(3,4-dihydroxy-5-nitrobenzylidene)-2,4-pentanedione, respectively. Entacapone and nitecapone are described in U.S. Pat. No. 5,446,194 as catechol-O-methyltransferase (COMT) inhibitors. Enteral and parenteral routes of administration are discussed in U.S. Pat. No. 5,446,194.

It is desirable that entacapone, nitecapone, or a pharmaceutically acceptable salt thereof, is released from the oral composition as soon as possible after ingesting it. This can normally be achieved by using a dissolution enhancing agent in the pharmaceutical composition. The dissolution enhancing agent may be a disintegrant or any other agent that enhances the dissolution. There is a vast selection of different dissolution enhancing agents, including disintegrants, on the market, which have different chemical and physical characteristics. When selecting the best dissolution enhancing agent to be used in a pharmaceutical composition in combination with an active agent, numerous factors have to be considered, e.g., the chemical and physical characteristics of the active agent and the dissolution enhancing agent, the chemical and physical characteristics of the auxiliary agents, such as diluents and binders, the method of preparing the composition, etc.

Croscarmellose sodium is a cross-linked polymer of carboxymethyl-cellulose sodium. According to the Handbook of Pharmaceutical Excipients (Ainley Wade and Paul J. Weller, Second Edition, The Pharmaceutical Press, London, 1994), it is used in oral pharmaceutical formulations as a disintegrant for tablets, capsules, and granules. Typically, concentrations from 0.5 to 5% w/w are used as a tablet disintegrant.

Neither the above-cited patent nor any other patent or publication of which applicants are aware describes an oral compacted composition comprising entacapone, nitecapone, or pharmaceutically acceptable salt thereof, and croscarmellose sodium.

SUMMARY OF THE INVENTION

Applicants have discovered that croscarmellose sodium is a superior disintegrant to be used in an oral compacted composition comprising entacapone, nitecapone, or pharmaceutically acceptable salt thereof. Accordingly, an object of the invention is to provide an oral compacted composition comprising entacapone, nitecapone, or a pharmaceutically acceptable salt thereof and croscarmellose sodium. The composition is premised on the discovery that croscarmellose sodium essentially increases the release rate of entacapone or nitecapone from an oral compacted composition. Particularly, an object of the invention is to provide an oral compacted composition comprising entacapone, nitecapone, or a pharmaceutically acceptable salt thereof and croscarmellose sodium, wherein the amount of croscarmellose sodium in the composition is at least 6% by weight, more preferably from about 8% to about 16% by weight, especially from about 10% to 14% by weight.

Preferably, the oral compacted composition is in the form of a tablet and, therefore, an object of the invention is to provide a tablet comprising entacapone, nitecapone, or a pharmaceutically acceptable salt thereof and croscarmellose sodium.

A further object of the invention is to provide a tablet comprising entacapone, nitecapone, or a pharmaceutically acceptable salt thereof and croscarmellose sodium, wherein the amount of croscarmellose sodium is at least 6% by weight, more preferably from about 8% to about 16% by weight, especially from about 10% to about 14% by weight.

An object of the invention is also to provide a method for preparing an oral compacted composition comprising entacapone, nitecapone, or a pharmaceutically acceptable salt thereof, and croscarmellose sodium, wherein said method comprises mixing a pharmaceutically effective amount of entacapone, nitecapone, or a pharmaceutically acceptable salt thereof, one or more auxiliary agents, and croscarmellose sodium to obtain a first mixture; compacting and crushing the first mixture one or more times to obtain a plurality of granules; adding a lubricant, a glidant or a mixture thereof to the granules to obtain a second mixture; and compressing the second mixture into a plurality of tablets.

An object of the invention is to provide a method of inhibiting catechol-O-methyltransferase by administering to a patient in need thereof an oral compacted composition comprising entacapone, nitecapone, or a pharmaceutically acceptable salt thereof.

A further aspect of the invention relates to the use of croscarmellose sodium in the manufacture of an oral compacted composition comprising entacapone, nitecapone, or a pharmaceutically acceptable salt thereof.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Figure 1:
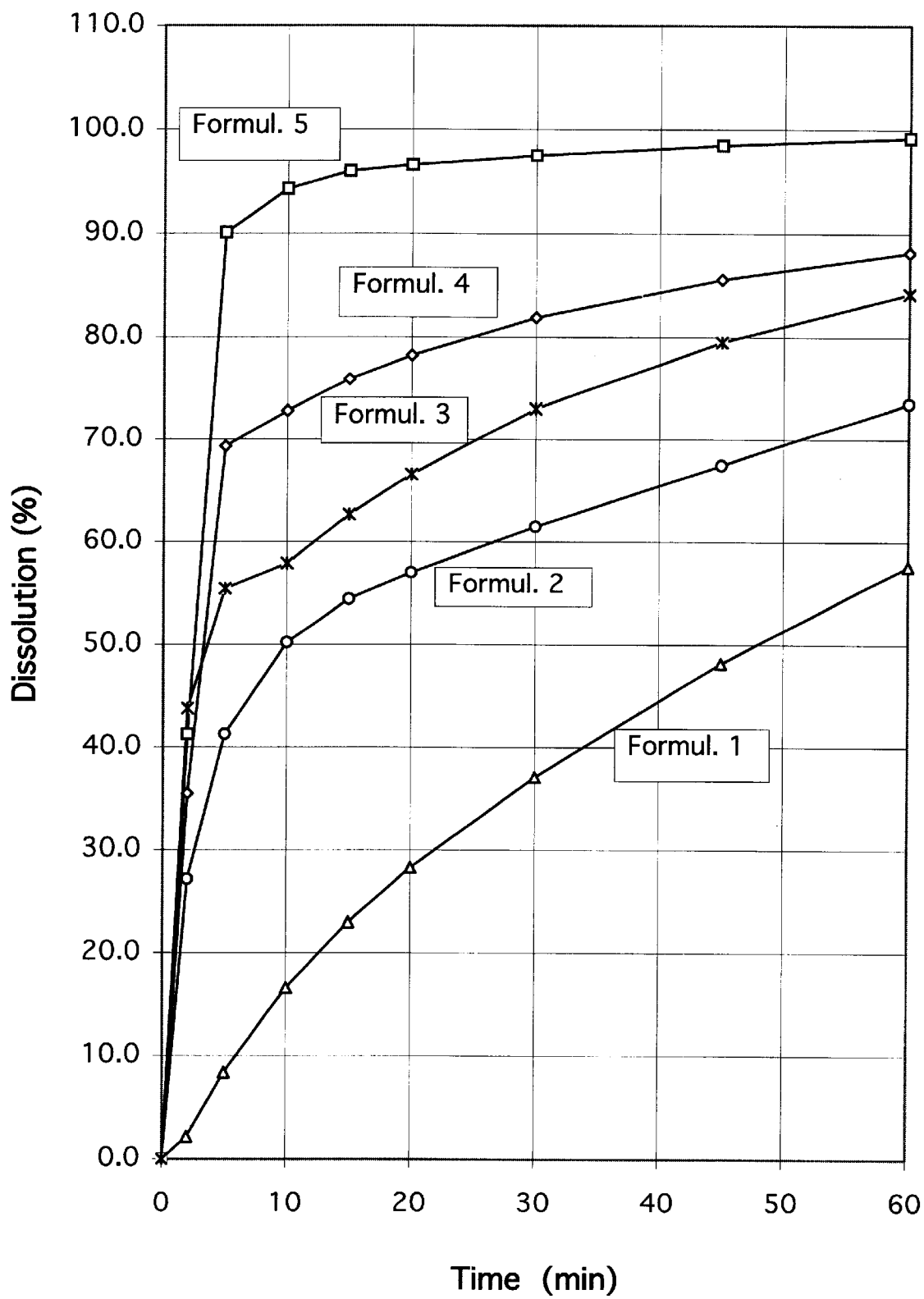
FIG. 1 shows the effect of different dissolution enhancing agents on the dissolution of compacted entacapone 200 mg tablet formulations.

Applicants have surprisingly discovered that croscarmellose sodium is effective for increasing the disintegration rate of an oral compacted composition comprising entacapone, nitecapone or a pharmaceutically acceptable salt thereof.

An oral compacted composition is a composition wherein a mixture of an active agent, one or more auxiliary agents and a dissolution enhancing agent is first compacted, then crushed into granules, and further the granules are tabletted or enclosed in a capsule. The best dissolution enhancing agent is the one that releases the active agent from the composition as fast as possible.

Applicants found that croscarmellose sodium is unexpectedly more efficient in releasing entacapone, nitecapone or a pharmaceutically acceptable salt thereof from an oral compacted composition than other common dissolution improving agents, such as starch, pregelatinized starch, microcrystalline cellulose, mannitol, sodium starch glycolate, or sodium lauryl sulphate. The dissolution test of Example 1 shows that 90.1% of entacapone is dissolved from a tablet comprising croscarmellose sodium as a disintegrant in 5 minutes (see FIG. 1). This result is far superior when compared to 69.3%, 55.4%, 41.3%, and 8.4% for sodium lauryl sulphate, sodium starch glycolate, pregelatinized starch, and mannitol containing tablets, respectively.

Croscarmellose sodium is in the oral compacted composition in an amount to enhance the dissolution of the active agent. Applicants have surprisingly discovered that the best dissolution results for the oral compacted compositions of the invention are achieved when the amount of croscarmellose sodium is far more than what is suggested in the art. Accordingly, it has been found that the amount of croscarmellose sodium in the oral compacted composition is preferably at least 6% by weight. More preferably, the amount of croscarmellose sodium is from about 8% to about 16% by weight, especially from about 10% to 14% by weight.

The amount of entacapone, nitecapone or a pharmaceutically acceptable salt thereof in the oral compacted composition is dependent on numerous factors known to one skilled in the art, such as, the type of mammal, the condition to be treated, the desired duration of use, etc. The compacted composition of the invention may also contain one or more other pharmaceutically active agents. The amount of entacapone in a tablet according to the invention can be about 5–400 mg, preferably about 100–200 mg, more preferably 200 mg.

Entacapone and nitecapone can be prepared, for example, as described in U.S. Pat. No. 5,446,194.

An oral compacted composition according to the invention can be prepared by mixing a pharmaceutically effective amount of entacapone, nitecapone, or a pharmaceutically acceptable salt thereof, one or more auxiliary agents and croscarmellose sodium and further compacting and crushing the mixture to form granules. The compacting and crushing can be proceeded one or more times. The granules are then mixed with a lubricant, a glidant or a mixture thereof and the mixture is compressed into tablets. The tablets may be coated after tabletting. The granules may also be encapsulated to form capsules. The auxiliary agent may be a diluent, a binder or a mixture of different diluents and/or binders. Preferably at least one of the auxiliary agents is water soluble. Suitable diluents and binders include, e.g., microcrystalline cellulose, hypromellose (HPMC), povidone, starch, lactose, sucrose, mannitol, sorbitol, etc. Suitable lubricants and glidants include, e.g., magnesium stearate, calcium stearate, hydrogenated vegetable oil, talc, colloidal silicon dioxide, etc.

One skilled in the art would recognize other suitable auxiliary agents, lubricants and glidants that can be used in the composition of the present invention.

The invention will be further clarified by the following examples, which are intended to be purely exemplary of the invention.

EXAMPLE 1

The dissolution of entacapone 200 mg tablet formulations containing different disintegrants were tested. The tablets were prepared by mixing, compacting, crushing and compressing as described above. The formulations were as described in Table 1. The dissolution of each formulation was tested using the basket method with a 100 rpm speed and 900 ml medium of phosphate buffer pH 5.8.

The amount of entacapone released was determined by a spectrophotometric method using a UVNIS spectrophotometer. The detection wavelength was 313 nm. The results, which are presented in FIG. 1, show that the formulation containg croscarmellose sodium (Formul. 5) releases entacapone fastest.

TABLE 1

Entacapone 200 mg tablet formulations containing different dissolution enhancing agents used in the dissolution test.

| Compound | Formul. 1 (mg) | Formul. 2 (mg) | Formul. 3 (mg) | Formul. 4 (mg) | Formul. 5 (mg) |
| --- | --- | --- | --- | --- | --- |
| Entacapone | 200 | 200 | 200 | 200 | 200 |
| Microcryst. cellulose | 50 | 210 | 410 | 420 | 370 |
| Mannitol | 400 | 0 | 0 | 0 | 0 |
| Pregelatinized Starch | 0 | 180 | 0 | 0 | 0 |
| Sodium Starch Glycolate | 0 | 0 | 40 | 0 | 0 |
| Sodium Lauryl Sulphate | 0 | 0 | 0 | 30 | 0 |
| Croscarmellose Sodium | 0 | 0 | 0 | 0 | 80 |
| Magnesium Stearate | 10 | 10 | 10 | 10 | 10 |

EXAMPLE 2

Figure 2:
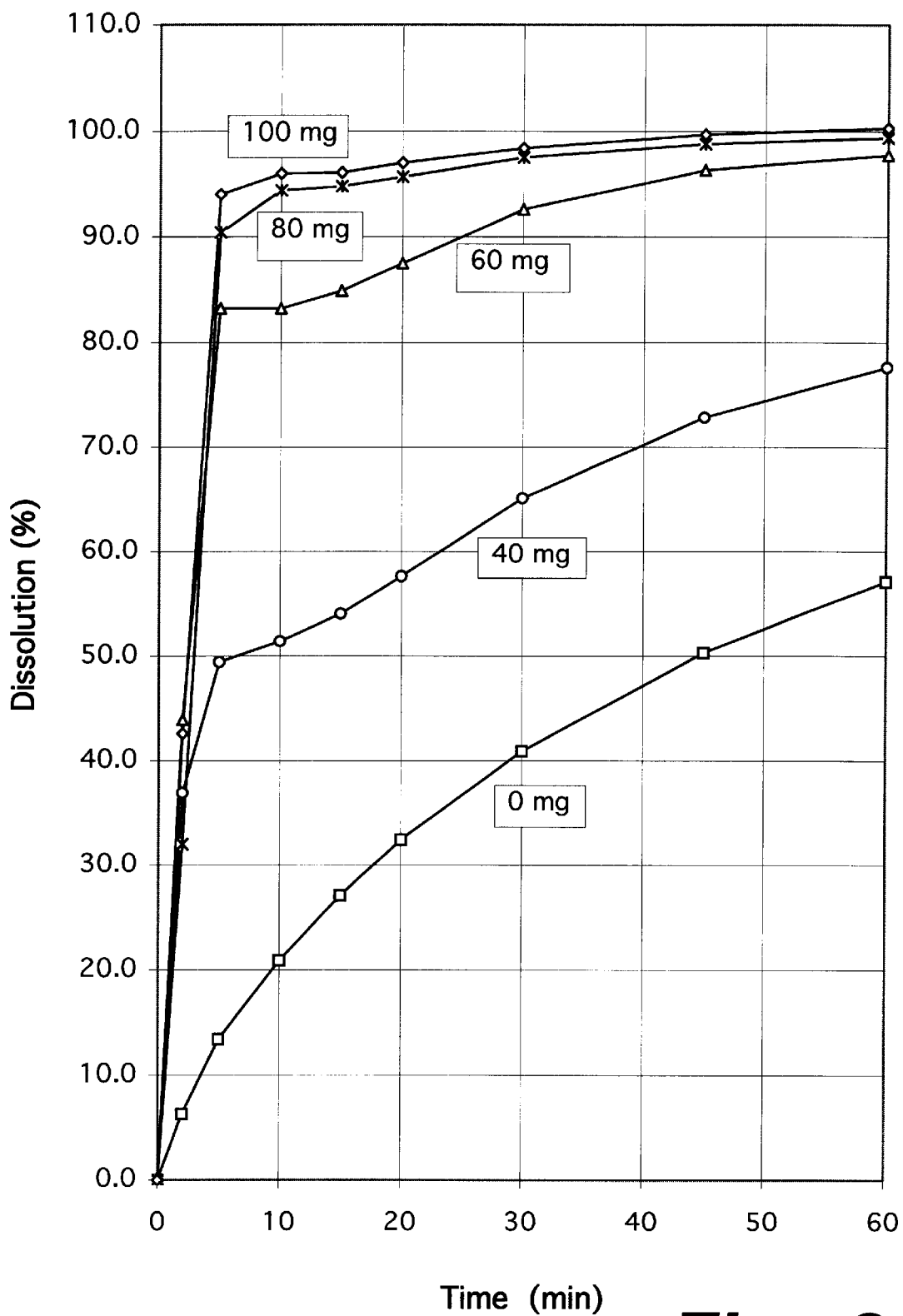
FIG. 2 shows the effect of croscarmellose sodium on the dissolution of compacted entacapone 200 mg tablet formulations.

The effect of croscarmellose sodium on the dissolution of compacted entacapone 200 tablet formulations was tested according to the method described in Example 1. The different formulations, i.e., Formul. 6-Formul. 10, are described in Table 2. The results of the dissolution test are shown in FIG. 2. The formulation containing the most croscarmellose sodium (100 mg) released entacapone the fastest.

TABLE 2

Compacted entacapone 200 mg tablet formulations containing different amounts of croscarmellose sodium.

| Compound | Formul. 6 (mg) | Formul. 7 (mg) | Formul. 8 (mg) | Formul. 9 (mg) | Formul. 10 (mg) |
| --- | --- | --- | --- | --- | --- |
| Entacapone | 200 | 200 | 200 | 200 | 200 |
| Microcryst. cellulose | 445 | 405 | 220 | 200 | 180 |
| Mannitol | 0 | 0 | 170 | 170 | 170 |

TABLE 2-continued

Compacted entacapone 200 mg tablet formulations containing different amounts of croscarmellose sodium.

| Compound | Formul. 6 (mg) | Formul. 7 (mg) | Formul. 8 (mg) | Formul. 9 (mg) | Formul. 10 (mg) |
| --- | --- | --- | --- | --- | --- |
| Croscarmellose Sodium | 0 | 40 | 60 | 80 | 100 |
| Magnesium Stearate | 15 | 15 | 12 | 12 | 12 |

EXAMPLE 3

Oral compact compositions according to the invention comprising entacapone as an active agent can include for instance those described in Table 3.

TABLE 3

Different oral compacted entacapone 200 mg tablet formulations.

| Compound | Formul. 11 (mg) | Formul. 12 (mg) | Formul. 13 (mg) | Formul. 14 (mg) | Formul. 15 (mg) |
| --- | --- | --- | --- | --- | --- |
| Entacapone | 200 | 200 | 200 | 200 | 200 |
| Microcrystalline cellulose | 290 | 230 | 160 | 190 | 120 |
| Sucrose | 10 | 0 | 100 | 60 | 190 |
| Mannitol | 90 | 160 | 80 | 140 | 50 |
| Hypromellose (HPMC) | 5 | 0 | 20 | 0 | 10 |
| Croscarmellose Sodium | 73 | 80 | 82 | 82 | 88 |
| Hydrogenated vegetable oil | 0 | 5 | 38 | 2 | 14 |
| Magnesium Stearate | 15 | 8 | 3 | 9 | 11 |

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The references discussed herein are specifically incorporated by reference in their entirety.

What is claimed is:

1. An oral compacted composition in the form of a tablet, which comprises a pharmaceutically effective amount of entacapone, nitecapone, or pharmaceutically acceptable salt of entacapone or nitecapone, and croscarmellose sodium in an amount of at least 6% by weight of the composition.

2. An oral compacted composition according to claim 1, which comprises entacapone or a pharmaceutically acceptable salt thereof.

3. An oral compacted composition according to claim 1, which comprises nitecapone or a pharmaceutically acceptable salt thereof.

4. An oral compacted composition according to claim 1, which comprises croscarmellose sodium in an amount of from about 8% to about 16% by weight of the composition.

5. An oral compacted composition according to claim 4, which comprises croscarmellose sodium in an amount of from about 10% to about 14% by weight of the composition.

6. An oral compacted composition according to claim 1, which comprises entacapone and about 6% by weight of croscarmellose sodium, and wherein the in vitro dissolution of entacapone is at least about 65% a over a period of about 30 minutes when measured using the basket method at 100 rpm speed and 900 ml medium of phosphate buffer at pH 58.

7. An oral compacted composition according to claim 1, which comprises entacapone and about 9% by weight of croscarmellose sodium, and wherein the in vitro dissolution of entacapone is at least about 92% over a period of about 30 minutes when measured using the basket method at 100 rpm speed and 900 ml medium of phosphate buffer at pH 5.8.

8. An oral compacted composition according to claim 2, which comprises from about 5 mg to about 400 mg of entacapone or pharmaceutically acceptable salt thereof.

9. An oral compacted composition according to claim 8, which comprises from about 100 mg to about 200 mg of entacapone or pharmaceutically acceptable salt thereof.

10. An oral compacted composition according to claim 9, which comprises about 200 mg of entacapone or pharmaceutically acceptable salt thereof.

11. An oral compacted composition in the form of a tablet, which comprises from about 100 mg or 200 mg of entacapone or pharmaceutically acceptable salt thereof, and croscarmellose sodium in an amount of at least 6% by weight of the composition.

12. A method for preparing an oral compacted composition in the form of a tablet wherein the composition comprises entacapone, nitecapone, or a pharmaceutically acceptable salt of entacapone or nitecapone, and the croscarmellose sodium in an amount of at least 6% by weight of the composition, which comprises:

a) mixing a pharmaceutically effective amount of entacapone, nitecapone, or pharmaceutically acceptable salt of entacapone or nitecapone, one or more auxiliary agents and croscarmellose sodium to obtain a first mixture;

b) compacting and crushing the first mixture one or more times to obtain a plurality of granules;

c) adding a lubricant, a glidant, or a mixture thereof to the granules to obtain a second mixture; and d) compressing the second mixture into a tablet.

13. A method according to claim 12, wherein the composition comprises croscarmellose sodium in an amount of from about 8% to about 16% by weight of the composition.

14. A method according to claim 13, wherein the composition comprises croscarmellose sodium in an amount of from about 10% to about 14% by weight of the composition.

15. A method according claim 12, wherein at least one of the auxiliary agents is water soluble.

16. A method according to claim 12, wherein the composition comprises from about 5 mg to about 400 mg of entacapone or pharmaceutically acceptable salt thereof.

17. A method according to claim 11, wherein the composition comprises from about 100 mg to about 200 mg of entacapone or pharmaceutically acceptable salt thereof.

18. A method according to the composition comprises about 200 mg of entacapone or pharmaceutically acceptable salt thereof.

19. A method of inhibiting catechol-O-methyltransferase, which comprises administering to a patient in need thereof an oral compacted composition according to claim 1.

20. A method according to claim 19, wherein the oral compacted composition comprises entacapone or a pharmaceutically acceptable salt thereof.

* * * * *

UNITED STATES PATENT AND TRADEMARK OFFICE
CERTIFICATE OF CORRECTION

PATENT NO. : 6,599,530 B2
DATED : July 29, 2003
INVENTOR(S) : Kari Vahervuo

It is certified that error appears in the above-identified patent and that said Letters Patent is hereby corrected as shown below:

Column 5,
Line 67, "65% a over" should read -- 65% over --.

Column 6,
Line 2, "pH 58." should read -- pH 5.8. --.
Line 35, "100 mg or 200 mg" should read -- 100 mg to 200 mg --.
Line 40, "tablet wherein" should read -- tablet, wherein --.
Line 6, "according claim" should read -- according to claim --.

Column 7,
Line 4, "claim 11," should read -- claim 16, --.
Line 7, "to the" should read -- to claim 17, wherein the --.

Signed and Sealed this

Eleventh Day of November, 2003

JAMES E. ROGAN
*Director of the United States Patent and Trademark Office*